(12) United States Patent
Blanken et al.

(10) Patent No.: US 9,590,442 B2
(45) Date of Patent: *Mar. 7, 2017

(54) CONTROL CIRCUITRY AND METHOD FOR CONTROLLING A BI-DIRECTIONAL SWITCH SYSTEM, A BI-DIRECTIONAL SWITCH, A SWITCHING MATRIX AND A MEDICAL STIMULATOR

(71) Applicant: Sapiens Steering Brain Stimulation BV, Eindhoven (NL)

(72) Inventors: Pieter Gerrit Blanken, Eindhoven (NL); Jeroen Jacob Arnold Tol, Eindhoven (NL); Franciscus Adrianus Cornelis Maria Schoofs, Eindhoven (NL); Dave Willem Van Goor, Eindhoven (NL)

(73) Assignee: Medtronic Bakken Research Center B.V., Maastricht (NL)

( * ) Notice: Subject to any disclaimer, the term of this patent is extended or adjusted under 35 U.S.C. 154(b) by 75 days.

This patent is subject to a terminal disclaimer.

(21) Appl. No.: 14/566,399

(22) Filed: Dec. 10, 2014

(65) Prior Publication Data

US 2015/0091533 A1 Apr. 2, 2015

Related U.S. Application Data

(63) Continuation of application No. 13/636,137, filed as application No. PCT/IB2011/051456 on Apr. 5, 2011, now Pat. No. 8,937,504.

(30) Foreign Application Priority Data

Apr. 12, 2010 (EP) .................................... 10159612

(51) Int. Cl.
*H02J 7/00* (2006.01)
*A61N 1/36* (2006.01)
(Continued)

(52) U.S. Cl.
CPC ............... *H02J 7/008* (2013.01); *A61N 1/05* (2013.01); *A61N 1/36185* (2013.01);
(Continued)

(58) Field of Classification Search
CPC ..................................................... H03K 17/063
See application file for complete search history.

(56) References Cited

U.S. PATENT DOCUMENTS 6,466,482 B2  10/2002  Shukuri et al.
6,559,689 B1   5/2003  Clark
(Continued)

FOREIGN PATENT DOCUMENTS

| JP | 11215835 A | 1/1896 |
|---|---|---|
| JP | 11215835 | 8/1999 |
| WO | 2004040761 A1 | 5/2004 |

OTHER PUBLICATIONS

Official Action dated Jul. 15, 2014 for Japanese Patent Application No. 2013-504365, 4 pp.
(Continued)

*Primary Examiner* — Hai L Nguyen
(74) *Attorney, Agent, or Firm* — Shumaker & Sieffert, P.A.

(57) ABSTRACT

A control circuitry (134) and a method for controlling a bi-directional switch (132) is provided. The bi-directional switch (132) having a control terminal (130) for receiving a control voltage (124) to control an on state and an off state of the bi-directional switch (132) and at least one semiconductor switch in a bi-directional main current path. The control circuitry (134) comprises an energy storage element (102), a coupling means (101) to couple the energy storage element (102) to a supply voltage to charge the energy storage element (102), and a control circuit (108) configured to receive power from the energy storage element (102) and
(Continued)

pendent of the supply voltage when the emergency storage element (102) is not coupled to the supply voltage. The coupling means (101) is configured for only coupling the energy storage element (102) to the supply voltage when the bi-directional switch (132) is in the off state.

13 Claims, 13 Drawing Sheets

(51) Int. Cl.
    *H03K 17/06*     (2006.01)
    *H03K 17/687*     (2006.01)
    *A61N 1/05*     (2006.01)
    *H02J 7/34*     (2006.01)

(52) U.S. Cl.
    CPC .......... *H02J 7/0052* (2013.01); *H03K 17/063* (2013.01); *H03K 17/687* (2013.01); *H02J 7/345* (2013.01)

(56) References Cited

U.S. PATENT DOCUMENTS

| | | | |
|---|---|---|---|
| 7,199,640 B2 | 4/2007 | De Cremoux et al. | |
| 8,618,864 B2 * | 12/2013 | Robbins | H01L 31/02021 |
| | | | 327/427 |
| 8,937,504 B2 | 1/2015 | Blanken et al. | |
| 2006/0022745 A1 | 2/2006 | Nakamura | |
| 2009/0184744 A1 | 7/2009 | Ricotti et al. | |
| 2010/0214006 A1 | 8/2010 | Hanazawa et al. | |

OTHER PUBLICATIONS

International Search Report from International Application No. PCT/IB2011/051456, dated Oct. 31, 2011.
Prosecution History for U.S. Appl. No. 13/636,137, from Mar. 26, 2014 through Sep. 11, 2014, 29 pp.
Examination from counterpart European Application No. 11717771.7, dated Oct. 8, 2015, 8 pp.

* cited by examiner

CONTROL CIRCUITRY AND METHOD FOR CONTROLLING A BI-DIRECTIONAL SWITCH SYSTEM, A BI-DIRECTIONAL SWITCH, A SWITCHING MATRIX AND A MEDICAL STIMULATOR

This application is a continuation of U.S. patent application Ser. No. 13/636,137 by Blanken et al., filed Sep. 20, 2012, now U.S. Pat. No. 8,937,504, and entitled "Control Circuitry and Method for Controlling a Bi-Directional Switch System, A Bi-Directional Switch, A Switching Matrix And A Medical Stimulator," which is a 371 National Stage of Patent Cooperation Treaty (PCT) Application No. PCT/IB2011/51456 by Blanken et al., filed on Apr. 5, 2011 and entitled "CONTROL CIRCUITRY AND METHOD FOR CONTROLLING A BI-DIRECTIONAL SWITCH SYSTEM, A BI-DIRECTIONAL SWITCH, A SWITCHING MATRIX AND A MEDICAL STIMULATOR," and which claims priority from European Patent Application No. 20100159612.0 by Blanken et al., filed Apr. 12, 2010 and entitled "CONTROL CIRCUITRY AND METHOD FOR CONTROLLING A BI-DIRECTIONAL SWITCH SYSTEM, A BI-DIRECTIONAL SWITCH, A SWITCHING MATRIX AND A MEDICAL STIMULATOR," the entire content of each of which is incorporated herein by reference.

FIELD OF THE INVENTION

The invention relates to the field of control circuitry for bidirectional switches.

BACKGROUND OF THE INVENTION

In the area of medical stimulators, there is a trend towards an increased number of stimulation electrode sites to improve therapeutic efficacy by accurate stimulation of the intended target volume using field steering. Besides stimulation, there is an increased demand for accurate sensing of neural activity. Both trends require the presence of a relatively large cross-point switch matrix to couple stimulation and/or sensing electronics to selected probe electrode sites. The available volume for energy storage is decreasing in the state-of-the-art medical stimulators, although the required energy for brain stimulation is substantially constant. Consequently, there is less room for a battery, and, thus, the circuitry of medical stimulator has to be a low power circuitry. The high number of switches of a cross-point switch matrix imposes an extremely-low power consumption requirement on a single switch with its control electronics.

The low-power requirement calls for integrated CMOS switches in a high-voltage IC technology, offering isolated NMOS and PMOS transistors. In state-of-the-art high-voltage IC technologies, the driving voltage of CMOS switches—the gate-to-source voltage—is limited to a few volts in comparison to the much higher voltage that is allowed across the CMOS switch itself—the drain-to-source voltage.

The article of W. N Reining, "A High voltage cross-point switch for medical applications", Digest of the 1999 IEEE Southwest Symposium on Mixed-Signal Design SSMSD '99, Tucson, Ariz., USA, Apr. 11-13, 1999, pp. 109-112, discloses in FIG. 2 a bidirectional switch and a control circuit for the bidirectional switch for medical applications, such as medical stimulators. Two NMOS transistors M10, M11 of which the gates and the sources are coupled to each other form the bidirectional switch.

A current source, built with a high-voltage PMOS transistor M2, is connected between the common gate of the bidirectional switch transistor and a voltage supply terminal VHI which receives a voltage that is higher than ever is appearing at the bidirectional switch I/O terminals. To turn the bidirectional switch on, the current source M2 is conducting a small current, according to the article 3 μA. The current is conducted by a string of diode-connected NMOS transistors M4, M5, M6 and a high voltage PMOS transistor M9. The gate of M9 is connected to the common source of the bidirectional switch and the drain is connected to a voltage supply terminal VSS which receives a voltage that is at a voltage lower than ever is appearing at the I/O terminals of the bidirectional switch. The voltage drops across the forward-biased diode-connected transistors M4, M5 and M6 and the gate-source voltage of M9, several volts, switch the bidirectional switch to the on-state. It is to be noted that, when the bidirectional switch is in the on-state, the circuit dissipates an amount of power which is the product of the value of the current times the voltage difference between the voltages on the terminals VSS and VHI.

A second current source is built with high-voltage NMOS transistor M8 and is connected between the common gate of the bidirectional switch transistors M10 and M11 and the voltage supply terminal VSS. To control the bidirectional switch to be in the off state, the current source built with M8 is conducting a small current, which is also conducted through high voltage NMOS transistor M3. The gate of M3 is connected to the common source of the bidirectional switch and the drain is connected to the voltage supply terminal VHI. The voltage drop between the gate and the source of M3 switches the bidirectional switch in the off state. If the bidirectional switch is in the off state, an amount of power is dissipated that equals the value of the current times the voltage difference between the voltages on the terminals VSS and VHI.

Thus, the control circuit of the bidirectional switch of the cited articles has a static power dissipation and the dissipation is irrespective of the state of the bidirectional switch.

SUMMARY OF THE INVENTION

It is an object of the invention to provide a control circuitry for a bidirectional switch which consumes less power than the known controlling circuitries.

A first aspect of the invention provides a control circuitry for controlling a bi-directional switch as claimed in claim 1. A second aspect of the invention provides a bi-directional switch system as claimed in claim 10. A third aspect of the invention provides a switching matrix as claimed claim 13. A fourth aspect of the invention provides a medical stimulator as claimed in claim 14. A fifth aspect of the invention provides a method of controlling a bi-directional switch as claimed in claim 15. Advantageous of embodiments are defined in the dependent claims.

A control circuitry for controlling a bi-directional switch in accordance with the first aspect of the invention comprises an energy storage element, a coupling means and a control circuit. The bi-directional switch has a control terminal for receiving a control voltage to control an on state and an off state of the bi-directional switch and has at least one semiconductor switch in a bi-directional main current path. The coupling means couples the energy storage element to a supply voltage for charging energy storage element. The energy storage element is only coupled to the supply voltage when the bi-directional switch is in the off state. The control circuit receives power from the energy storage element and supplies the control voltage having a voltage level being independent of the supply voltage when the energy storage element not coupled to the supply voltage.

The control circuit receives power from the energy storage element and, thus, the control circuit is able to generate a control voltage which is related to the voltage across the energy storage element. The bi-directional switch receives the control voltage on the control terminal. To reliably switch on or switch bi-directional switch, the control voltage needs to have a voltage in specific voltage ranges, which is not directly related to supply voltage. When the energy storage element is not coupled to the supply voltage, the control circuit is able to generate the control voltage which does not directly relate to the supply voltage, because the voltages of the terminals of the energy storage element may float to required voltage levels. However, when the energy storage element is being charged, the voltages of the terminals of the energy storage element become connected to fixed voltage levels, which may prevent the control circuit of generating a control voltage which may reliably switch the bi-directional switch on or off. Consequently, the energy storage element is only charged when the bi-directional switch is in the off state.

It is to be noted that the bi-directional switch mainly forms a capacitive load to the control circuitry because the load is formed by a gate of at least one semiconductor switch which has to be charged or discharged to switch from the conducting non-conducting state or vice versa. Thus, the bi-directional switch does not form a static power load for the control circuitry.

The coupling means and the control circuit may be implemented as a low power semiconductor circuit which only consumes power at the instants at which the transistors of the semiconductor circuitry switch to another state. The obtaining of the control voltage does not rely on currents that flow permanently. Thus, the control circuitry does not have a static power consumption.

The control circuitry does not have a static power consumption and the bi-directional switch does not statically consume power via the control terminal. Hence, the invention according to the first aspect is more power efficiently than the known circuitries.

In an embodiment, the bi-directional switch further has at least one semiconductor switch in a bi-directional main current path and a reference voltage output terminal for providing a reference voltage indicating to which voltage level the control voltage on the control terminal has to be defined to enable switching of the bi-directional switch. The control circuitry further comprises a reference voltage input terminal for receiving the reference voltage from the reference voltage output terminal. The energy storage element has a first terminal and a second terminal. The coupling means comprises a first switch arranged between the first terminal and a first supply voltage terminal to receive a first supply voltage, a second switch arranged between the second terminal and a second supply voltage terminal to receive a second supply voltage, and a further control circuit. The further control circuit controls at least one of the first switch and the second switch to be open or closed and only closes at least one of the first switch and the second switch when the bi-directional main current path of the bi-directional switch is in the off state. When both the first switch and the second switch are closed, the energy storage element is charged to a voltage being a difference between the first supply voltage and the second supply voltage. When both the first switch and the second switch are open, the voltages of the first terminal and the second terminal are floating to obtain a floating state of the energy storage element. The control circuit comprises power supply terminals that are coupled between the first terminal and the second terminal to receive power supply energy from the energy storage element. The control voltage is generated in a floating manner when the energy storage element is in the floating state.

The control circuit receives a supply voltage from the first terminal and the second terminal and, thus, the control circuit is able to generate a control voltage which is directly related to the voltage of the first terminal or the voltage of the second terminal. The control voltage may have a value in a range limited by the voltage of the first terminal and the voltage of the second terminal. When the energy storage element is in the floating state, the control voltage floats as well.

The bi-directional switch has at least one semiconductor switch in the main current path. Such a semiconductor switch can only be closed when a control voltage is received which is high enough, or low enough, compared to the reference voltage. In an embodiment, the reference voltage input terminal may be coupled to the second terminal, thus, when the energy storage element is in the floating state, the reference voltage determines the voltage level of the second terminal, and consequently, the level of the first terminal. Thus, if the control circuitry receives the reference voltage, the control circuit is able to generate the control voltage with respect to the reference voltage such that the bi-directional switch may be opened or closed independently of the first supply voltage and the second supply voltage which are used to charge the energy storage element. In another embodiment, the reference voltage input terminal may be coupled to the control circuit such that the control circuit may directly generate the control voltage with respect to the voltage level of the reference voltage.

It is to be noted that the bi-directional switch forms mainly a capacitive load to the control circuitry because the load is formed by a gate of the at least one semiconductor switch which has to be charged or discharged to switch from the conducting to the non-conducting state or vice versa. Thus, the bi-directional switch does not form a static power load for the control circuitry. Only when the bi-directional switch is in the on state, a current flows through the bi-directional main current path which may result in a small power dissipation in the main current path. However, this power dissipation in the main current path is not a load for the control terminal, because the control terminal only needs to charge or discharge the gate of the at least one semiconductor switch. Changing the state of the bi-directional switch from the conductive to the non-conductive state and/or vice versa leads to power dissipation in the control circuit during the transition. This well-known dynamic power dissipation can not be avoided. The energy required is taken from the energy stored in the energy storage element.

The control circuit operates on basis of supply power received from the energy storage element. In order to store energy in the energy storage element and to obtain a voltage across the energy storage element, the energy storage element has to be charged. By connecting the first terminal and the second terminal via the first switch and the second switch to the first supply voltage terminal and the second supply voltage terminal, respectively, energy is stored in the energy storage element. When the first switch and/or the second switch are closed, the voltage of the first terminal and the voltage of the second terminal do not float anymore and the control voltage is not generated in the floating manner. The non-floating control voltage can not reliable switch the at least one semiconductor switch of the bi-directional switch, and, thus, the charging of the energy storage element may only be performed when the bi-directional switch is in the off state.

The further control circuit and the control circuit may be implemented as a low power semiconductor circuit which only consumes power at the instants at which the transistors of the semiconductor circuitry switch to another state. The obtaining of the control voltage does not rely on currents that flow permanently. Thus, the control circuitry does not have static power consumption.

The control circuitry does not have a static power consumption and the bi-directional switch does not statically consume power via the control terminal. Hence, the invention according to the first aspect is more power efficient than the known circuitries.

In an embodiment the bi-directional switch is always open in a predefined time period of iterating cycles. This knowledge may be used by the further control circuit to close the first switch and the second switch during the interval of which is a-priori known that the bi-directional switch is not closed.

In another embodiment, the further control circuit is coupled to the control circuit for receiving an indication whether the bi-directional switch is in the off-state. On basis of the received indication the further control circuit may decide whether the first switch and the second switch may be closed or not.

In another embodiment, the control circuit comprises a latch. The latch memorizes the on state or the off state of the bi-directional switch and supplies the control voltage according to the memorized state.

It is advantageous to have a latch which memorizes the on or off state of the bi-directional switch, because it does not require the continuous receiving of a signal which indicates the on or the off state. Such a signal with on/off information may be provided for a limited time period and subsequently the latch memorizes the provided information. Especially it prevents the discharging of the energy storage element when the bi-directional switch is switched to the off state because the bi-directional switch is decoupled from the energy storage element. This increases power efficiency.

In an embodiment, the control circuit comprises an input terminal for receiving a switch control signal which indicates a required on or off state of the bi-directional switch. In other words, the received switch control signal is used by the control circuit to generate the control voltage such that the bi-directional switch opens or closes as indicated by the switch control signal. Other circuitry, for example, some circuitry of an apparatus which comprises the control circuitry according to the invention, may generate the switch control signal.

In a further embodiment, the control circuit is coupled to the first supply voltage terminal and/or the second supply voltage terminal. The input terminal is configured to receive the switch control signal which relates to at least one of the first supply voltage and the second supply voltage. The control circuit further comprises a communication channel circuit to communicate the switch control signal to a floating control signal having a voltage related to the voltage of the first terminal and/or the second terminal.

In other words, the provided switch control signal is not a floating voltage and is, for example, a voltage in a voltage range limited by the first supply voltage and the second supply voltage. Such a switch control signal may be received from a circuitry which receives power from the first supply voltage and the second supply voltage. The voltage of the provided switch control signal has to be translated into a voltage which is directly related to the floating voltage, for example, to a voltage in a voltage range limited by the voltage of the first terminal and the voltage of the second terminal. The communication channel circuit performs the translation. The translation has to be performed because the control signal is also related to the floating voltages of the first terminal and/or the second terminal. To perform the translation, the control circuit may receive the first supply voltage and/or the second supply voltage such that the communication channel may determine how the received switch control signal exactly relates to the first supply voltage and/or the second supply voltage. It is to be noted that the function of the communication channel is the level-shifting of the switch control signal to another level and that this function does not necessarily require a connection to the first supply voltage terminal and/or the second supply voltage terminal. In other embodiments the communication channel is connected to terminals which have a fixed voltage different from the first supply voltage terminal and/or the second supply voltage terminal.

The embodiment is advantageous because it allows the receiving of a bi-directional switch control signal that is related to the first supply voltage and/or the second supply voltage which means that a circuitry which provides this signal does not have to be aware of the floating voltages in the control circuitry. The control circuit may compare the received bi-directional switch control signal with the first supply voltage and/or the second supply voltage to interpret the bi-directional switch control signal. In an example, the bi-directional control signal may substantially equal the first voltage to indicate that the bi-directional switch has to be in the on state, and may substantially equal the second voltage to indicate that that the bi-directional switch has to be in the off state.

In a further embodiment, the latch of the control circuit stores the on state of the bi-directional switch in response to receiving a set signal and stores the off state of the bi-directional switch in response to receiving a reset signal. The bi-directional switch control signal comprises a set sub-signal and a reset sub-signal. The communication channel circuit communicates both the set sub-signal and the reset sub-signal to the latch.

With the use of a set and a reset signal, the setting of the state of the latch requires only temporarily a signal in the form of a set signal or a reset signal. Because of the limitation in time, the communication channel circuit only has to perform the translation from a voltage related to the first supply voltage and/or the second supply voltage towards a voltage related to the voltage of the first terminal and/or the voltage of the second terminal during limited time periods. Thus, the communication channel circuit consumes a limited amount of power and the power efficiency of the control circuitry is increased.

In another embodiment, the energy storage element is a storage capacitor which is manufactured on basis of a MOS transistor of which the drain, the source and the backgate are electrically connected to each other and form together a first electrode of the storage capacitor, and the gate of the MOS transistor forms the second electrode of the capacitor.

In other words, the gate oxide of a MOS transistor is used as the dielectric of the storage capacitor. Using the gate oxide as the dielectric is advantageous because it allows the integration of the storage capacitor in a semiconductor technology, and prevents the use of an external storage capacitor which has to be connected to the circuitry by means of external ports.

The storage capacitor has to store a small amount of energy which is enough to open and/or close the bi-directional switch once or multiple times in between the time intervals during which the storage capacitor is charged. It is expected that, when the storage capacitor is always charged when the bi-directional switch is open, the storage capacitor has only to store energy which is enough for closing and subsequently opening the bi-directional switch only once. Thus, the amount of stored energy is relatively small and thus the size of the storage capacitor may be relatively small which is advantageous in the context of integrating the storage capacitor in the semiconductor technology. However, the capacitor may be constructed in another suitable manner.

In an embodiment, the first switch or the second switch is a bootstrap diode, and the other one of the first switch and the second switch is a MOS transistor. The conducting or non-conducting state of the MOS transistor is controlled by the further control circuit.

The bootstrap diode has to be connected between the first terminal and the first supply voltage terminal, or between the second terminal and the second supply voltage terminal such that the bootstrap diode cannot conduct a current when the energy storage element is in the floating state and that it can conduct the current when the energy storage element is not in the floating state. Only when the voltage of the first terminal is connected via a conducting MOS transistor to the first supply voltage, or when the voltage of the second terminal is connected via a conducting MOS transistor to the second supply voltage, the energy storage element is not in the floating state, and, thus, the energy storage element receives energy via the MOS transistor and via the bootstrap diode. The use of one MOS transistor and one bootstrap diode is an efficient solution because the diode is a relatively cheap and relatively simple component. It is to be noted that the bootstrap diode is not an active switch, but acts as a passive switch which becomes conducting when the voltage across the diode (the anode—cathode voltage) is larger than the (forward) threshold voltage of the diode. If the first switch and the second switch are implemented according to this embodiment, the further control circuit only directly controls the MOS transistor to be in the on state and thereby indirectly controls the other switch, implemented as the bootstrap diode.

In another embodiment, the first switch is a first MOS transistor and the second switch is a second MOS transistor. The further control circuit controls a conducting or a non-conducting state of the first MOS transistor as well as a conducting or a non-conducting state of the second MOS transistor.

The use of two MOS transistors is an efficient and effective solution for creating the first switch and the second switch and provides full control with respect to the floating or non-floating state of the energy storage element and with respect to the charging of the energy storage element and also avoids the voltage drop of a forward-biased diode, when the switch is, for example, implemented as a bootstrap diode. Thus, if two MOS transistors are used, the energy storage element may be charged to a voltage level which is substantially equal to the difference voltage of the first supply voltage and the second supply voltage.

In accordance to the second aspect of the invention, a bi-directional switch system is provided which comprises a bi-directional switch and the control circuitry according to the first aspect of the invention. The bi-directional switch provides the same benefits as the control circuitry according to the first aspect of the invention and has similar embodiments with similar effects as the corresponding embodiments.

In an embodiment, the bi-directional switch comprises a main current path between a first I/O terminal and a second I/O terminal and further comprises a first MOS transistor and a second MOS transistor in the main current path. The first MOS transistor and the second MOS transistor have a common source and a common gate. A drain of the first MOS transistor is coupled to the first I/O terminal and a drain of the second MOS transistor is coupled to the second I/O terminal. The common gate is coupled to the control terminal.

Using two MOS transistors in the main current path of a bi-directional switch is an effective and efficient solution by which the main current path may be opened or closed.

In an embodiment the common source is coupled to the reference voltage output terminal of the bi-directional switch.

Thus, when the energy storage element is in the floating state, the floating voltage of the second terminal follows the voltage of the common source of the first MOS transistor and the second MOS transistor. Especially when the bi-directional switch is in the on state, the voltage of the common source is in a range which is limited by the voltage of the first I/O terminal and the voltage of the second I/O terminal. Thus, when, for example, a sinus signal is transmitted through the bi-directional switch, the voltages of the first I/O terminal and the second I/O terminal are continuously varying, and, consequently, the voltage of the common source varies accordingly, as well as the floating voltage of the second terminal. The voltage of the first terminal is related to the voltage of the second terminal via the energy storage element, and consequently varies also according to the voltage of the common source as well. Thus, the control voltage that is generated by the control circuit may be used to switch the first MOS transistor and the second MOS transistor in the off or the on state because the generated control voltage relates to the voltage of the common source.

According to a third aspect of the invention, a switching matrix is provided which comprises at least one bi-directional switch system according to the second aspect of the invention at least one junction point of the matrix. Such a switching matrix, for example, may be a cross-point matrix used to couple electrodes of a medical stimulator to signal generators and/or measurement circuits.

According to a fourth aspect of the invention, a medical stimulator is provided which comprises at least one bi-directional switch system according to the second aspect of the invention.

The switching matrix and the medical stimulator provide the same benefits as the bi-directional switch according to the second aspect of the invention and have similar embodiments with similar effects as the corresponding embodiments.

According to a fifth aspect of the invention, a method of controlling a bi-directional switch is provided. The bi-directional switch has a control terminal for receiving a control voltage to control an on and off state of the bi-directional switch and at least one semiconductor switch in a bi-directional main current path. The method comprises a first step of coupling an energy storage element to a supply voltage only when the bi-directional switch is in the off state for charging the energy storage element. In another step the method receives power from the energy storage element. In a further step the method supplies the control voltage having a voltage level being independent of the supply voltage when the energy storage element is not coupled to the supply voltage.

The method according to the fifth aspect of the invention provides the same benefits as the control circuitry according to the first aspect of the invention and has similar embodiments with similar effects as the corresponding embodiments of the circuitry.

In an embodiment of the method of controlling the bi-directional switch, the bi-directional switch has at least one semiconductor switch in a bi-directional main current path, a control terminal to control an on and off state of the bi-directional main current path, and a reference voltage output terminal for providing a reference voltage indicating to which voltage level a signal on the control terminal has to relate. The method comprises a first step of receiving a first supply voltage at a first supply voltage terminal and receiving a second supply voltage at a second supply voltage terminal. The method comprises a further step of controlling by means of a first control circuit a first switch and a second switch both to be closed only when the bi-directional switch is in the off state. The first switch is arranged between the first supply voltage terminal and a first terminal of an energy storage element and the second switch is arranged between the second supply voltage terminal and a second terminal of the energy storage element. The method comprises another step of controlling by means of the first control circuit the first switch and the second switch both to be open to obtain the energy storage element in a floating state. The method comprises a further step of receiving the reference voltage of the bi-directional switch at a reference voltage terminal which is coupled to the second terminal. The method comprises also the step of receiving the voltage of the first terminal and the second terminal at power supply terminals of a second control circuit. And the method comprises the step of generating a control voltage at an output terminal of the second control circuit. The output terminal is coupled to the control terminal of the bi-directional switch. The control voltage is generated in a floating manner when the energy storage element is in a floating state.

These and other aspects of the invention are apparent from and will be elucidated with reference to the embodiments described hereinafter.

It will be appreciated by those skilled in the art that two or more of the above-mentioned embodiments, implementations, and/or aspects of the invention may be combined in any way deemed useful.

Modifications and variations of the system, and/or of the method which correspond to the described modifications and variations of the system, can be carried out by a person skilled in the art on the basis of the present description.

Figure 1A:
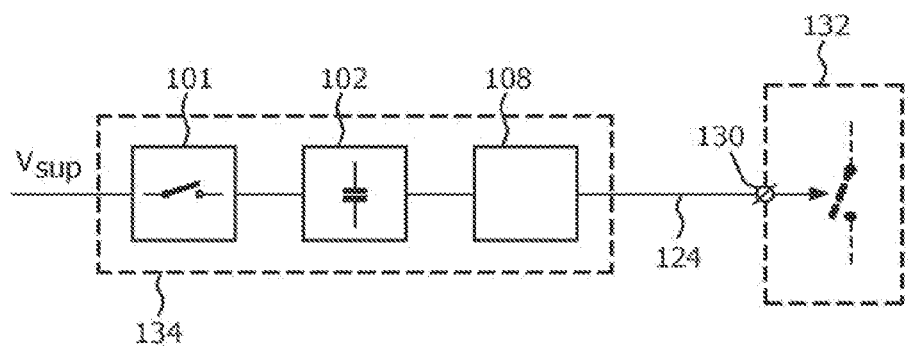
FIG. 1a schematically shows an embodiment of the control circuitry according to the first aspect of the invention, FIG. 1b schematically shows another embodiment of the control circuitry according to the first aspect of the invention, FIG. 2a schematically shows an embodiment of the control circuitry and of the bi-directional switch wherein the bi-directional switch comprises two NMOS transistors, FIG. 2b schematically shows an embodiment of the control circuitry and of the bi-directional switch wherein the bi-directional switch comprises two PMOS transistors, FIG. 3 schematically shows two embodiments of an energy storage element, FIG. 4a schematically shows an embodiment of the first switch and of the second switch, FIG. 4b schematically shows another embodiment of the first switch and of the second switch, FIG. 5a schematically shows a first embodiment of a communication channel, FIG. 5b schematically shows a second embodiment of a communication channel, FIG. 6a schematically shows a third embodiment of a communication channel, FIG. 6b schematically shows a fourth embodiment of a communication channel, FIG. 6c schematically shows a fifth embodiment of a communication channel, FIG. 7a schematically shows a circuit of a latch and a circuit which is coupled in between the latch and a communication channel, FIG. 7b schematically shows another circuit of a latch and another circuit which is coupled in between the latch and a communication channel, FIG. 8 schematically shows an additional circuit which may be coupled between a latch and the bi-directional switch, FIG. 9 schematically shows another embodiment of the bi-directional switch, FIG. 10 schematically shows the embodiment of FIG. 9 inclusive parasitic diodes, FIG. 11 schematically shows an embodiment of a bi-directional switch according to the second aspect of the invention, FIG. 12 schematically shows an embodiment of a switching matrix according to the third aspect of the invention, FIG. 13 schematically shows an embodiment of a medical stimulator according to the fourth aspect of the invention, and FIG. 14 schematically shows an embodiment of a method according to the fifth aspect of the invention.

It should be noted that items denoted by the same reference numerals in different Figures have the same structural features and the same functions, or are the same signals. Where the function and/or structure of such an item have been explained, there is no necessity for repeated explanation thereof in the detailed description.

The figures are purely diagrammatic and not drawn to scale. Particularly for clarity, some dimensions are exaggerated strongly.

DETAILED DESCRIPTION OF THE EMBODIMENTS

A first embodiment is shown in FIG. 1a. A control circuitry 134 for controlling a bi-directional switch 132 is shown. The bi-directional switch 132 comprises a control terminal 130 to receive a control voltage 124 to control an on state and an off state of the bi-directional switch 132. The control circuitry 134 comprises an energy storage element 102, a coupling means 101 and a control circuit 108. The coupling means 101 couples the energy storage element 102 to a supply voltage $V_{sup}$ to charge the energy storage element 102. The coupling means 101 only couples the energy storage element 102 to the supply voltage $V_{sup}$ when the bi-directional switch 132 is in the off state. The control circuit 108 receives power from the energy storage element 102 and supplies the control voltage 124 which has a voltage level that is independent of the supply voltage $V_{sup}$ when the energy storage element 102 is not coupled to the supply voltage $V_{sup}$.

Figure 1B:
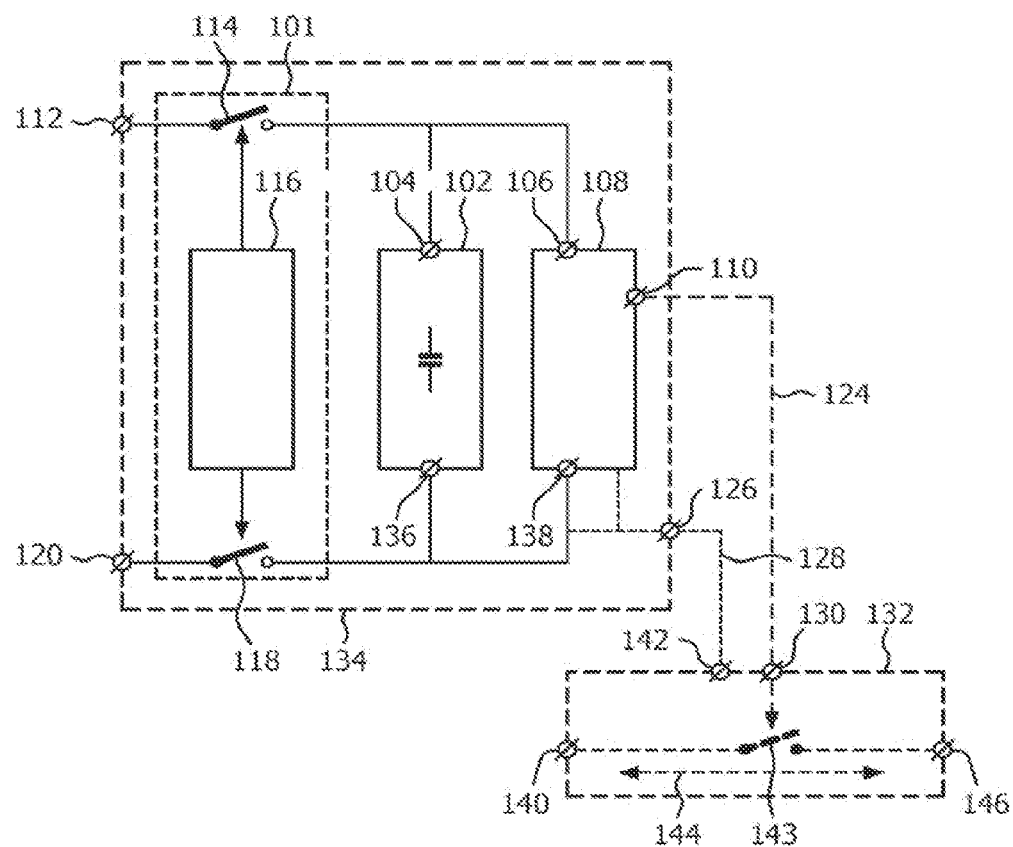

Another embodiment is shown in FIG. 1b. A schematic drawing of an embodiment of a control circuit 134 is shown which is connected to a bi-directional switch 132 which is also drawn schematically. The bi-directional switch 132 has a bi-directional main current path 144 between a first I/O terminal 140 and a second I/O terminal 146. At least one controllable semiconductor switch 143 is provided in the bi-directional main current path 144. The bi-directional switch 132 as a control terminal 130 for controlling an on state and an off state of the bi-directional main current path 144. The bi-directional switch 132 has further a reference voltage output terminal 142 for providing a reference voltage 128 which indicates to which voltage level a received control voltage on the control terminal 130 has to be defined to enable switching of the bi-directional switch. Thus, depending on the voltage difference between the reference voltage and the control voltage received at the control terminal 130, the bi-directional switch 132 is controlled in the on or in the off state.

The control circuitry 134 comprises a first supply voltage terminal 112 for receiving a first supply voltage and has a second supply voltage terminal 120 for receiving a second supply voltage. The control circuitry 134 further comprises an energy storage element 102 having a first terminal 104 and a second terminal 136. A first switch 114 is arranged between the first supply voltage terminal 112 and the first terminal 104. A second switch 118 is arranged between the second supply voltage terminal 120 and the second terminal 136. The control circuitry 134 further comprises a further control circuit 116 which controls the first switch 114 and the second switch 118 to be open or closed. When both the first switch 114 and the second switch 118 are closed the energy storage element 102 is charged to a voltage being a difference voltage between the first supply voltage and the second supply voltage. When both the first switch 114 and the second switch 118 are open, the voltages of the first terminal 104 and the second terminal 136 are floating and consequently a floating state of the energy storage element 102 is obtained.

The control circuitry 134 further comprises a control circuit 108 for generating a control voltage 124 at an output terminal 110 of the control circuit 108. The control voltage 124 is supplied to the control terminal 130 of the bi-directional switch. The control circuit 108 has power supply terminals 106, 138 to receive power supply energy from the energy storage element 102. Thus, power supply terminal 106 is coupled to the first terminal 104 and power supply terminal 138 is coupled to the second terminal 136. The control voltage 124 is generated in a floating manner when the energy storage element 102 is in the floating state. Thus, the generated control voltage 124 relates to the voltage of the first terminal 104 and/or of the second terminal 136. In an example, the voltage level of the control voltage 124 is in a range that is limited by the voltage of the first terminal 104 and the voltage of the second terminal 136.

The control circuitry 134 further has a reference voltage input terminal 126. The reference voltage input terminal 126 receives a reference voltage 128 from the reference voltage output terminal 142.

In an embodiment, the reference voltage terminal is coupled to the control circuit 108 such that the control circuit 108 may generate the control voltage 124 which is defined with respect to the received reference voltage 128

In another embodiment, the reference voltage terminal is coupled to the second terminal 136. Thus, if the energy storage element 102 is in the floating state, the received reference voltage 128 determines the voltage of the second terminal 136. Subsequently, the energy storage element 102 determines the voltage difference between the first terminal 104 and the second terminal 136, and thus, the voltage of the first terminal 104 relates also to the reference voltage 128 if the energy storage element 102 is in the floating state. The control circuit 108 receives at its power supply terminals 106, 138 the voltages of the first terminal 104 and the second terminal 136, and, consequently, the generated control voltage 124 primarily relates to the voltages of the first terminal 104 and the second terminal 136, and thus, the generated control voltage 124 is defined with respect to the reference voltage 128. When the energy storage element 102 is in the floating state, the voltage difference between the reference voltage 128 and the control voltage 124 determines the on or off state of the bi-directional switch 132.

The further control circuit 116 of the control circuitry 134 only closes the first switch 114 and/or the second switch 118 when the main current path 144 of the bi-directional switch 132 is in the off state. If the first switch 114 or the second switch 118 is closed, the voltage of the first terminal 104 or the second terminal 136, respectively, is not floating anymore. This means that the generated control voltage 124 does not float anymore. The bi-directional switch 132 can only be closed reliably when the received control voltages 124 relates to the reference voltage 128 and not to the fixed first supply voltage or the fixed second supply voltage. Thus, the first switch 114 and/or the second switch 118 may only be closed when the bi-directional switch 132 is in the off state. In order to charge the energy storage element 102, both the first switch 114 and the second switch 118 have to be closed.

The further control circuit 116 may have predefined knowledge about the time intervals during which the bi-directional switch 132 is in the off state. The bi-directional switch 132 may be open during predefined intervals of iterating cycles and as such the further control circuit 116 may close the first switch 114 and/or the second switch 118 during the predefined intervals.

Figure 2A:
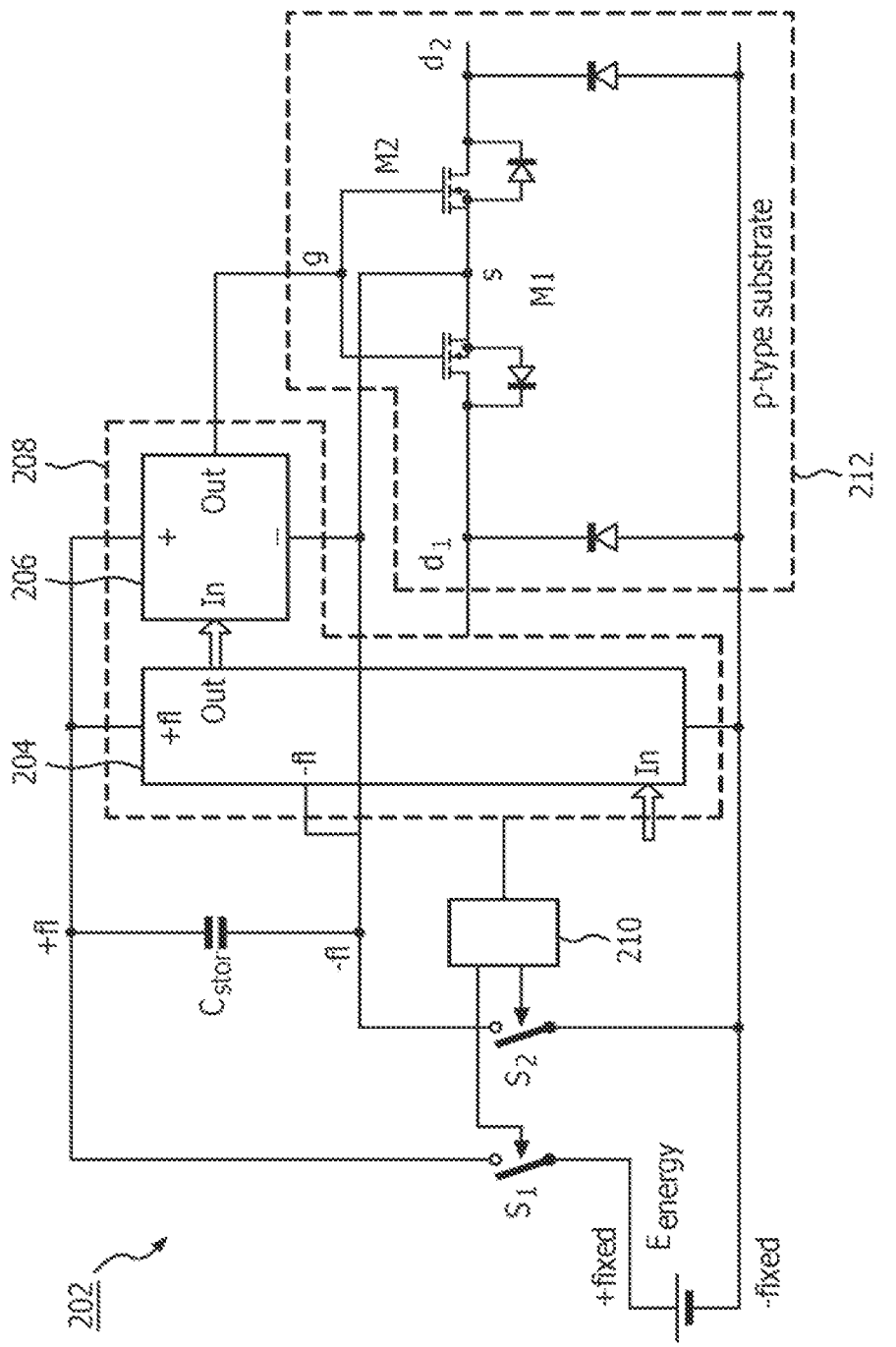

FIG. 2a schematically shows an embodiment 202 of a control circuitry and a bi-directional switch 212 which may be manufactured in p-type substrate semiconductor technology. The bi-directional switch 212 is implemented with two NMOS transistors M1, M2 which are placed in an anti-series configuration, which means that they have a common gate g and a common source s. A drain d1 of one of the MOS transistors M1, M2 is a first I/O terminal of the bi-directional switch 212 and a drain d2 of the other one of the MOS transistors M1, M2 is a second I/O terminal of the bi-directional switch 212.

The control circuitry comprises a first switch S1, a second switch S2, a storage capacitor $C_{stor}$, a first controller 210 and a second controller 208. A voltage supply $E_{energy}$ provides a first voltage +fixed and a second voltage −fixed which is lower than the first voltage +fixed. The first switch receives the first voltage +fixed and provides, when the first switch S1 is closed, the first voltage +fixed to a first terminal of the storage capacitor. The voltage of the first terminal is indicated in the figure with +fl. The second switch S2 receives the second voltage −fixed and provides, when the second switch S2 is closed, the second voltage −fixed to a second terminal of the storage capacitor. The voltage of the second terminal is indicated in FIG. 2a with −fl.

When both the switches S1 and S2 are closed, the storage capacitor $C_{stor}$ is charged to obtain, when the storage capacitor $C_{stor}$ is completely charged, a voltage difference between the first terminal and the second terminal of the storage capacitor $C_{stor}$ which is substantially equal to the voltage of the voltage supply $E_{energy}$. When both the switches S1 and S2 are open, the voltages +fl, −fl of the first terminal and of the second terminal, respectively, are floating. It is to be noted that it is not essential that the switches S1 and S2 are closed sufficiently long to completely charge the capacitor $C_{stor}$. It is sufficient to charge the capacitor $C_{stor}$ to a voltage level which is required for providing the control circuit 206 with sufficient supply power to be able to control the bi-directional switch 212.

The second terminal is connected to the common source s of the bi-directional switch 212 and as such the voltage of the common source s and the voltage of the second terminal −fl follow each other. When the bi-directional switch 212 is in the on state the voltage of the common source s is in between the voltage of the first I/O terminal d1 and of the second I/O terminal d2. At such moments the switches S1 and/or S2 may not be closed, otherwise the voltage of the second terminal may be in conflict with the voltage of the common source s. Thus, when the bi-directional switch 212 is in the on state, none of the switches S1 and S2 may be closed, and only when the bi-directional switch 212 is in the off state, the switches S1 and/or S2 may be closed.

The opening and closing of switches S1 and S2 is controlled by a further control circuit 210. In an embodiment, the bi-directional switch 212 is always in the off state during predefined intervals of successive cycles, and predefined knowledge of these predefined intervals of successive cycles may be available in the further control circuit 210 such that the further control circuit 210 only closes the switches S1 and/or S2 during the predefined intervals.

The control circuitry further comprises the control circuit 208 which comprises a communication channel 204 and a latch 206. Both the communication channel 204 and the latch 206 receive a power supply voltage from the storage capacitor $C_{stor}$. The communication channel is further connected to the second supply voltage −fixed. The communication channel receives an input signal at an input port In which indicates whether the bi-directional switch has to be in the on state or in the off state. The received input signal has a voltage level which relates to the first voltage +fixed and/or relates to the second voltage −fixed, for example, the voltage level of the input signal is in a range limited by the first voltage +fixed and by the second voltage −fixed. The communication channel translates the received input signal to an output signal of the communication channel which has a voltage level which relates to the voltage level +fl of the first terminal and/or to the voltage level −fl of the second terminal, for example, a voltage level in a range which is limited by the voltage level +fl and the voltage level −fl. The output signal of the communication channel 204 is used to set or reset the latch 206 to a specific state and the latch 206 provides a control voltage to the common gate g according to the state of the latch 206.

The generated control voltage relates to the voltage level +fl of the first terminal and/or the voltage level −fl of the second terminal and because the second terminal is coupled to the common source s a desired control voltage is generated by the latch 206 such that the gate-source-voltage of the NMOS transistors M1 and M2 is such that the bi-directional switch 212 is closed or opened. If the control voltage is higher than the threshold voltage of the NMOS transistors M1 and M2, the bi-directional switch 212 is in the on-mode. Thus, the latch 206 may provide a control voltage which is close to the voltage level +fl of the first terminal when the bi-directional switch 212 had to be in the on state and the latch 206 may provide a control voltage which is close to the voltage level −fl of the second terminal when the bi-directional switch 212 had to be in the off state.

In an embodiment, the further control circuit 210 is coupled to the control circuit 208 to receive an indication when the bi-directional switch is controlled to be in an off state. This indication is used by the further control circuit 210 to decide whether the first switch S1 and/or the second switch S2 may be closed or should be open.

Figure 2B:
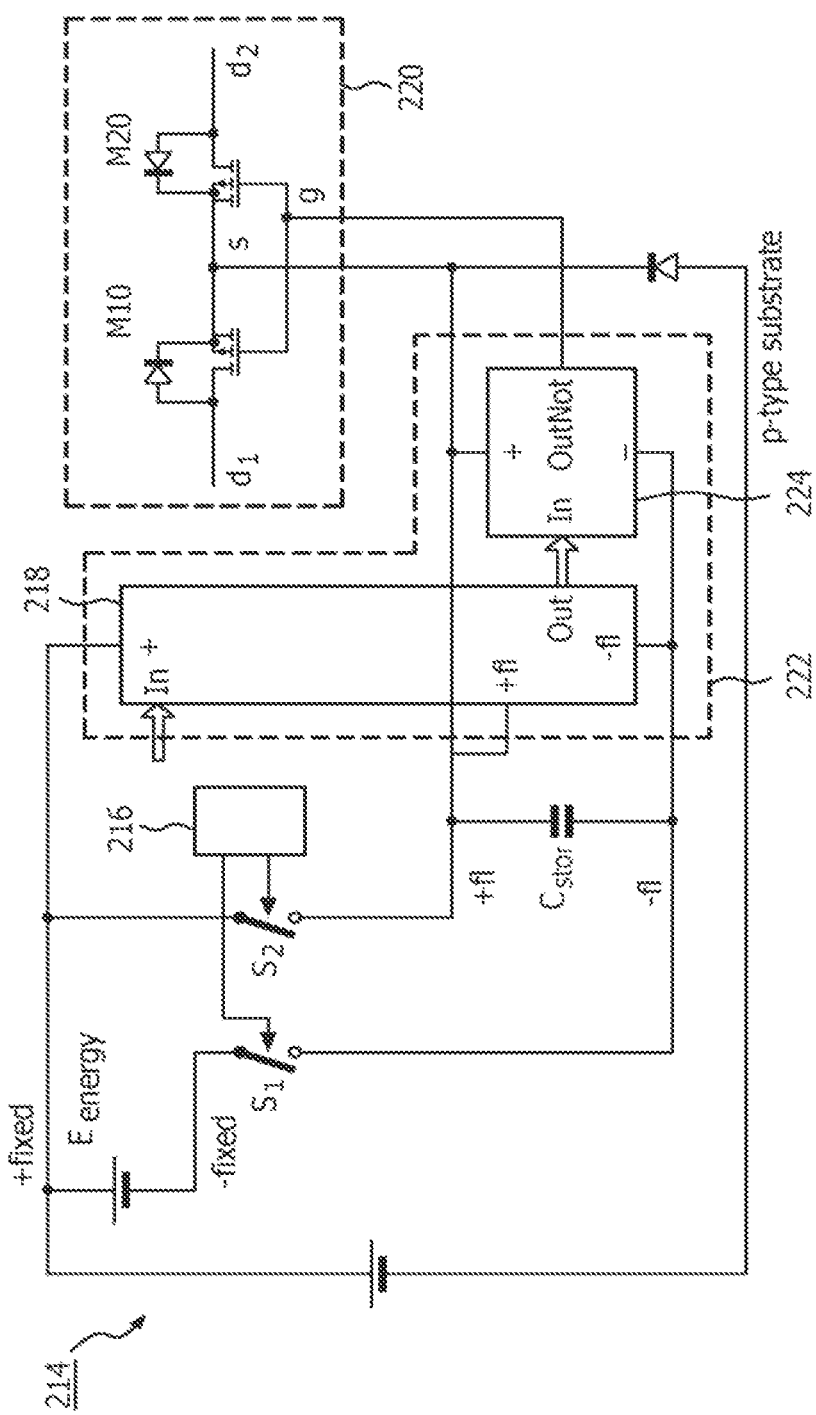

In FIG. 2b another embodiment 214 of the bi-directional switch 220 and of the control circuitry is schematically drawn. The embodiment is similar to the embodiment of FIG. 2a, however, the bi-directional switch 220 comprises two PMOS transistors M10, M20 and thus the latch 224 has to provide a control voltage which the inverse of the control voltage of the embodiment of FIG. 2a, because the bi-directional switch 220 is closed when the voltage of a common gate g of the PMOS transistors M10, M20. The first controller 216, the latch 224 and the communication channel 218 (latch 224 and communication channel 218 being collectively identified by reference numeral 222) are similar to the first controller 210, the latch 206, and the communication channel 204 of the embodiment of FIG. 2a.

Figure 3:
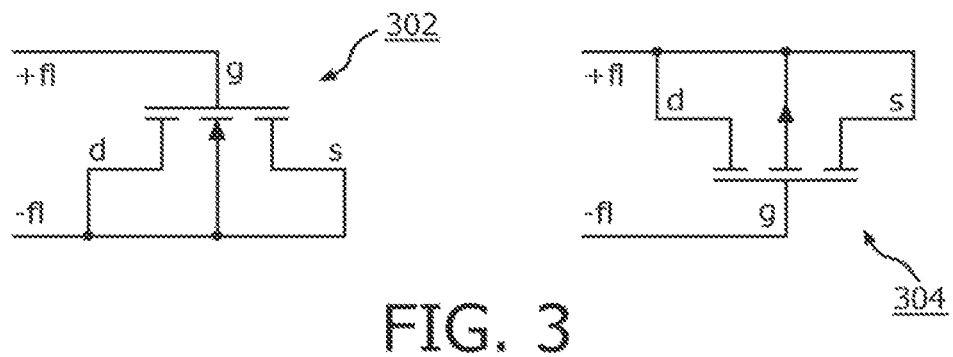

In FIG. 3 two schematic embodiments of energy storage elements 302, 304 are presented. The energy storage element may be implemented as a storage capacitor, which may be manufactured in a semiconductor technology by means of a NMOS transistor 302 or a PMOS transistor 304. The source s, the drain d and the backgate of both the NMOS transistor 302 and the PMOS transistor 304 form a first electrode of the storage capacitor and the gate g forms the second electrode. Thus, the gate-oxide forms the dielectric of the storage capacitor. Other embodiments of a storage capacitor implemented in a semiconductor technology are a so-termed Metal-Insulator-Metal (MIM) capacitor and a so-termed fringe-capacitor. The MIM capacitor is manufactured on basis of a first electrode in one of the standard metal layers of the metal-layer-stack of the semiconductor device, on top of which a thin layer of an insulating material is deposited whereon a second metal electrode is manufactured. The fringe-capacitor comprises two interdigitated electrodes manufactured in one metal layer of the semiconductor device or manufactured in two or more neighboring metal layers of the semiconductor device. The finger-shaped parts of the first electrode form a capacitance together with the finger-shaped parts of the second electrode. It is to be noted that the discussed embodiments of the energy storage elements are meant to be manufactured in a semiconductor technology, which is advantageous in order to obtain a single device which comprises the complete control circuitry. However, the energy storage element may also be manufactured on a separate semiconductor device. For example, in a three dimensional semiconductor arrangements, a first semiconductor device may comprise the logic of the control circuitry and may comprise contacts at the top surface of the first semiconductor device, and a second semiconductor device which is arranged to be placed on the top surface of the first semiconductor device comprises the energy storage element. Especially, for example, in switching matrix semiconductor devices it may be advantageous to manufacture the energy storage elements in a separate semiconductor device which is placed on top of a semiconductor device comprising the switching logic such that larger switching matrices may be manufactured.

Figure 4A:
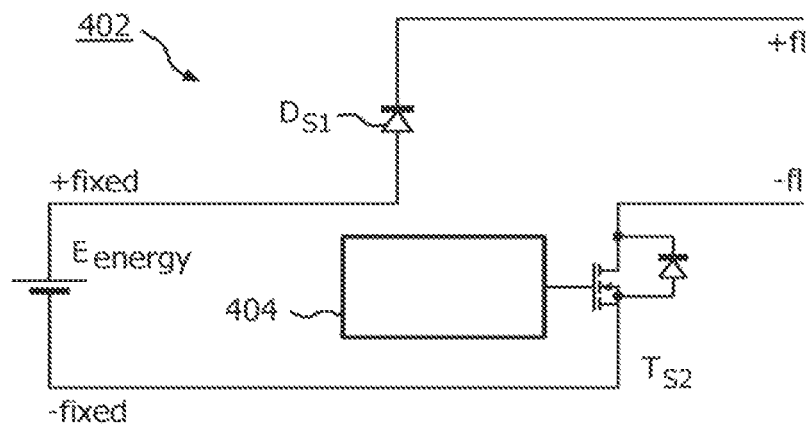

In FIG. 4a a first embodiment 402 of the first switch and the second switch is presented. The second switch is formed by an NMOS transistor $T_{S2}$ of which the conducting state is controlled by a further control circuit 404. Especially if the second switch is controlled to be in the conducting state, the voltage level −fl of the second terminal becomes substantially equal to the second supply voltage −fixed. The voltage level +fl of the first terminal drops to a level below the first supply voltage +fixed, because it is expected that the energy storage element is not fully charged anymore. The first switch is formed by a bootstrap diode $D_{S1}$. If the first supply voltage +fixed is higher than the voltage level +fl of the first terminal, the bootstrap diode becomes conductive and the energy storage element is charged. After a short period of time, apart from the voltage drop across the forward-biased diode, the voltage level of the +fl of the first terminal becomes substantially equal to the first supply voltage +fixed. It is to be noted that the conducting and non-conducting state of the bootstrap diode is not directly controlled by the further control circuit 404, however, by controlling the second switch to be in the conducting state, the state of the bootstrap diode is indirectly controlled by the further control circuit 404.

Figure 4B:
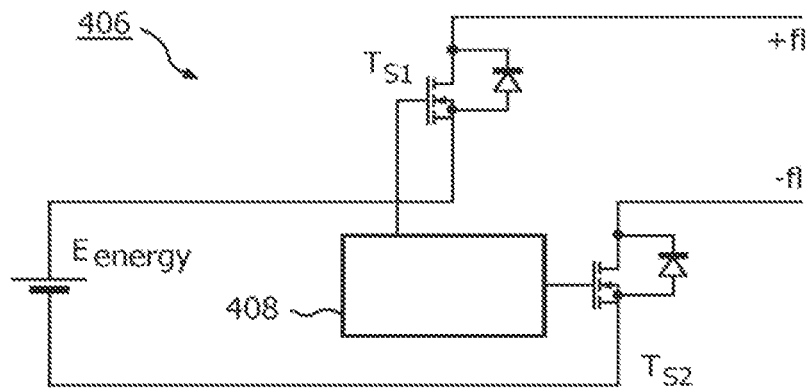

In FIG. 4b a second embodiment 406 of the first switch and the second switch is presented. The first switch and the second switch are implemented as NMOS transistors $T_{S1}$, $T_{S2}$ of which the conducting or non-conducting state is controlled by a further control circuit 408. When both NMOS transistors $T_{S1}$, $T_{S2}$ are controlled to be in the conducting state the capacitor is charged from the voltage supply $E_{energy}$.

Figure 5A:
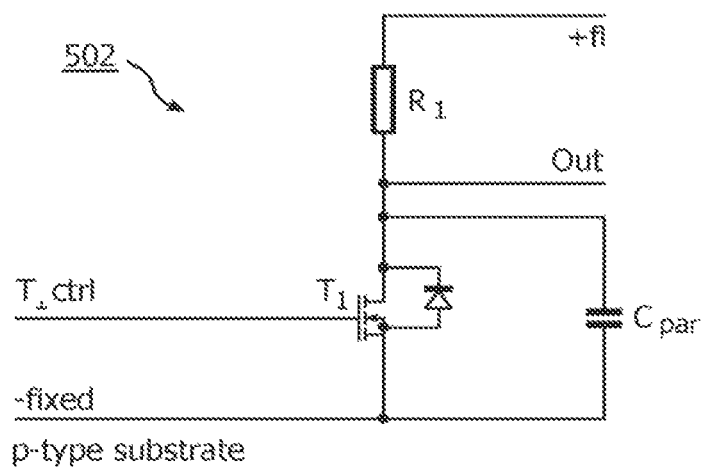

In FIG. 5a an embodiment of a communication channel 502 is presented. The signal $T_1$ctrl is a bi-directional switch control signal that is received by the control circuit and indicates a desired on or off state of the bi-directional switch. The signal $T_1$ctrl is connected to the gate of NMOS transistor T1. The communication channel further receives the first supply voltage −fixed and the voltage +fl of the first terminal. The $T_1$ctrl signal has a voltage level which relates to the first supply voltage −fixed. The output terminal Out of the communication channel provides a translated bi-directional switch control signal which has a voltage level which relates to the voltage +fl of the first terminal.

The conducting state of transistor T1 is controlled by the $T_1$ctrl signal. If transistor T1 does not conduct, the output voltage at the output terminal Out is substantially equal to the voltage +fl. If the transistor T1 conducts, a current flows through the resistor R1 and the transistor T1, and a voltage drop across resistor R1 determines how much the output voltage at the output terminal Out is below the voltage +fl. Thus, the signal of the output terminal Out relates to the floating voltage +fl.

The voltage swing of the output terminal Out has to be obtained by an accurate parameterization of the components of the circuit 502. The voltage swing depends on, for example, the threshold voltage of T1, the current gain factor of T1, the resistance of R1, etc.

Figure 5B:
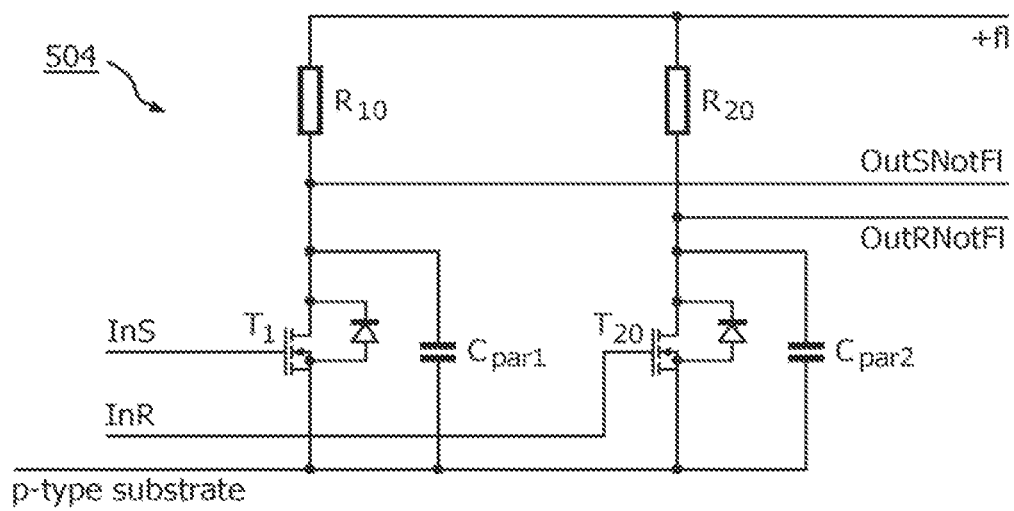

FIG. 5b presents another embodiment of a communication channel 504. In the embodiment the bi-directional switch control signal which is received by the control circuit comprises a set sub-signal InS and a reset sub-signal InR. Both signals are translated to a voltage level which relates to the floating voltage +fl with two communication channel sub-circuits which are similar to the embodiment of FIG. 5a. Set (InS) and Reset (InR) signals are used to set or reset the state of the latch, respectively, and thereby controlling the state of the bi-directional switch. To control the state of the latch, the Set (InS) and Reset (InR) signals have only to be provided for a relatively short period of time. Only during the relatively short period of time a current flows through the resistors R10, R20 and the transistors T1 and T20. Thus, the communication channel only consumes power when the bi-directional switch has to be switched to another state. Hence, the communication channel does not consume static power.

Figure 6A:
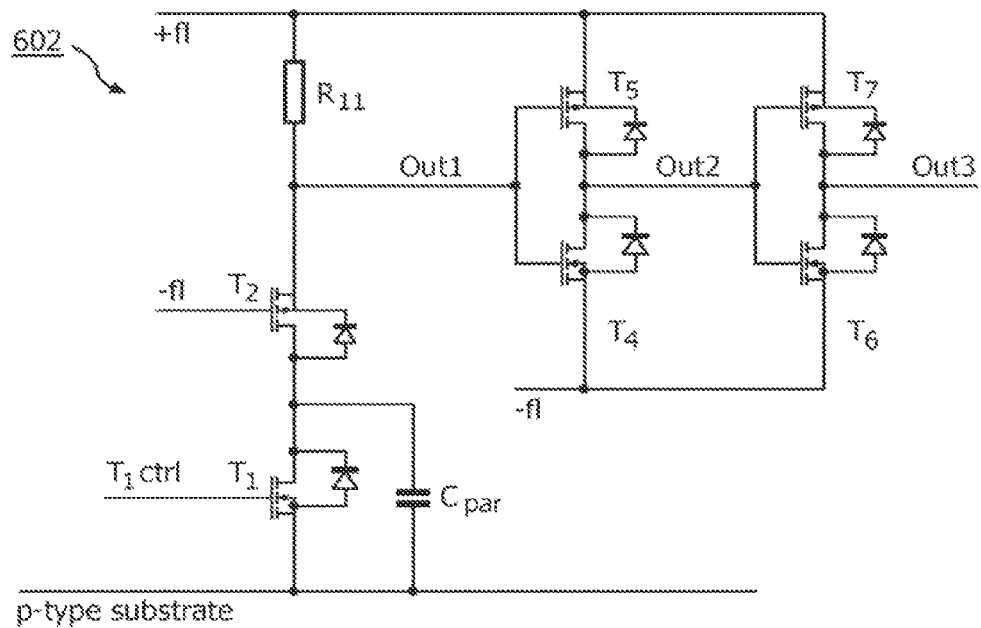

In FIG. 6a another embodiment of one half the communication channel 602 is presented. When a set sub-signal and a reset sub-signal are received by the control circuit, the circuit 602 has to be implemented twice, once for translating the set sub-signal to a signal related to the voltage levels −fl and +fl, and once for translating the reset sub-signal to a signal related to the voltage levels −fl and +fl.

The communication channel 602 is an improved communication channel compared to the embodiments 502 and 504 of FIG. 5a and FIG. 5b, respectively. The communication channel 602 has a better output voltage swing between the floating voltages +fl and −fl of the first terminal and the second terminal respectively. A (high-voltage) PMOS transistor $T_2$ is added in the branch that links the fixed voltages +fixed and −fixed to the floating voltages +fl and −fl. An input transistor $T_1$ is normally switched off. Resistor $R_{11}$ pulls node Out1 towards the voltage level +fl. PMOS transistor $T_2$ is highly conductive, as its gate is tied to −fl, so an interconnected drains of $T_1$ and $T_2$ also show the +fl voltage. Two inverter stages $T_4/T_5$ and $T_6/T_7$ provide a normally-high output node Out3, and all three branches do not dissipate. When a gate of the input transistor $T_1$ is pulled high (implying the reception of a set or reset sub-signal) a conductive channel of $T_1$ pulls the interconnected drains of $T_1$ and $T_2$ down, and also the Out1 node comes dawn. A resistance of $R_1$ is chosen such that without $T_2$ the input transistor $T_1$ would easily pull the Out1 node below the local negative supply rail −fl. By introducing $T_2$, this is no longer possible, as $T_2$ would be switched off. The resulting voltage at the Out1 node is slightly above the floating voltage −fl, namely at least a PMOS threshold voltage. The inverter stage $T_4/T_5$ now has a relatively low voltage at its input, but NMOS $T_4$ probably will not be switched off completely. The widths and lengths of $T_4$ and $T_5$ have to be selected such that the output node Out2 is pulled high (requiring a relatively weak NMOS $T_4$ and a relatively strong PMOS $T_5$). Inverter stage $T_6/T_7$ creates a logic "low" at the output Out3. As long as $T_1$ is activated the two left-hand branches may dissipate and the inverter stage $T_6/T_7$ does not show static dissipation. As noted before, $T_1$ is only active during the relatively short time intervals during which a set or reset sub-signal is received.

Figure 6B:
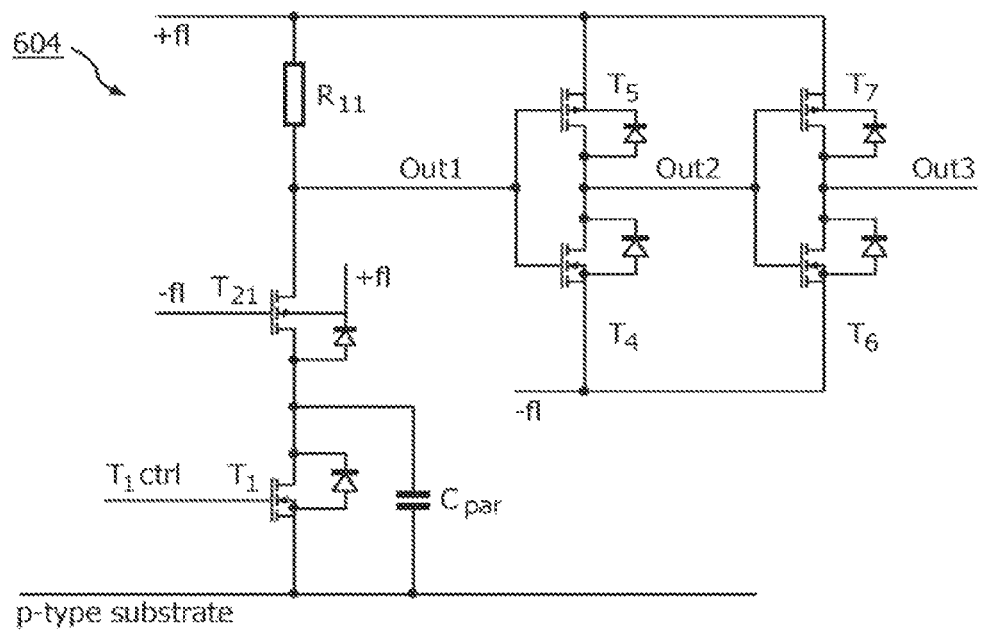

In the embodiment 602 of FIG. 6a a source-to-backgate junction of PMOS transistor T2 is shorted, which reduces the threshold voltage and thus creates a voltage of node Out1 relatively close to the floating voltage −fl. However, a disadvantage is the requirement to use an additional high-voltage island in the semiconductor device for $T_2$, which increases the parasitic capacitance to the substrate and decreases the high-frequency rejection. In the communication channel 604 of FIG. 6b a backgate terminal of PMOS transistor T21 is connected to the (floating) voltage level +fl. The extra high-voltage island is avoided at the cost of increased threshold voltage of T21 when T1 is activated. Node Out1 does not get as close to the voltage level −fl anymore as in the embodiment 602 of FIG. 6a. The widths and lengths of T4 and T5 need to be adapted to still make sure that the output node Out2 is pulled high, which requires an even weaker NMOS T4 and even stronger PMOS T5.

Figure 6C:
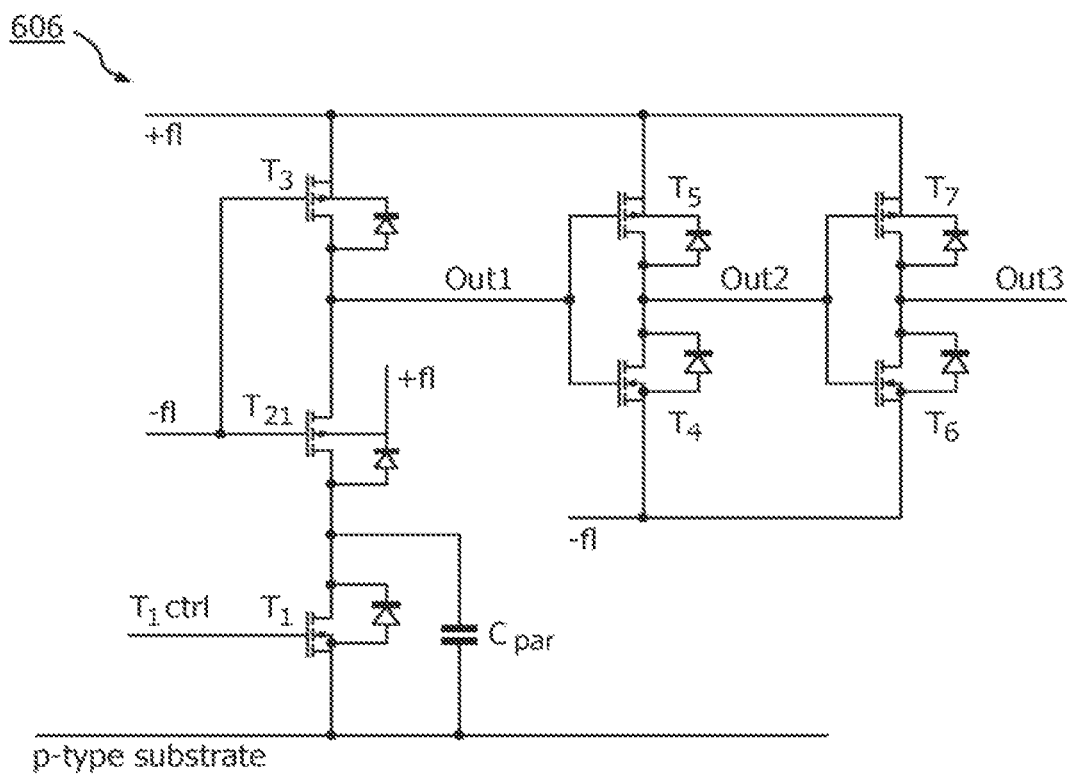

In the circuit of FIG. 6c a further embodiment 606 of the communication channel is depicted. Resistor R11 of the embodiment 604 of FIG. 6b has been replaced by a PMOS transistor T3 of which the gate is connected to the (floating) voltage level −fl. Transistor T3 acts as a non-linear resistance. Resistances use a relatively large area of the semiconductor device, while the transistor T3 may be manufactured at a much smaller size.

Figure 7A:
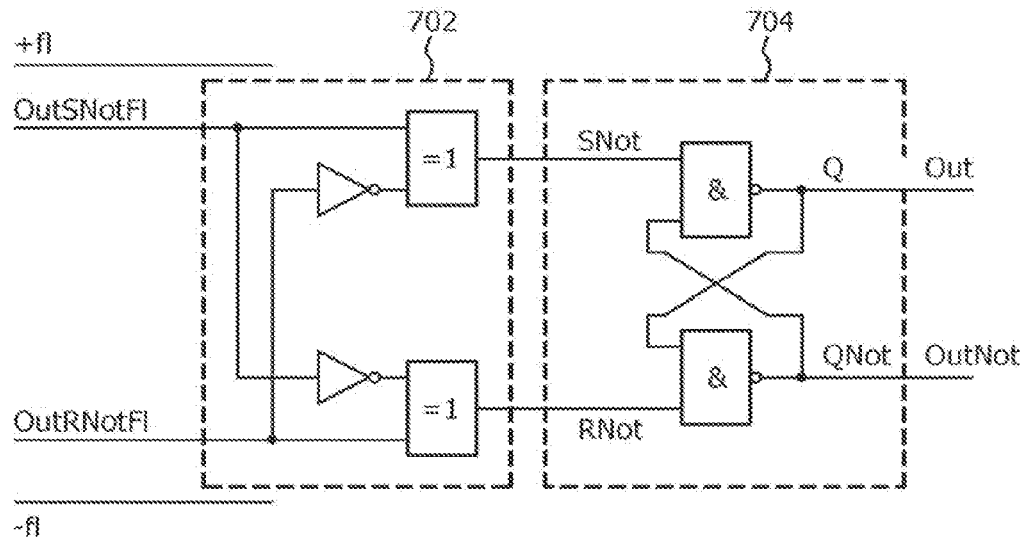
Figure 7B:
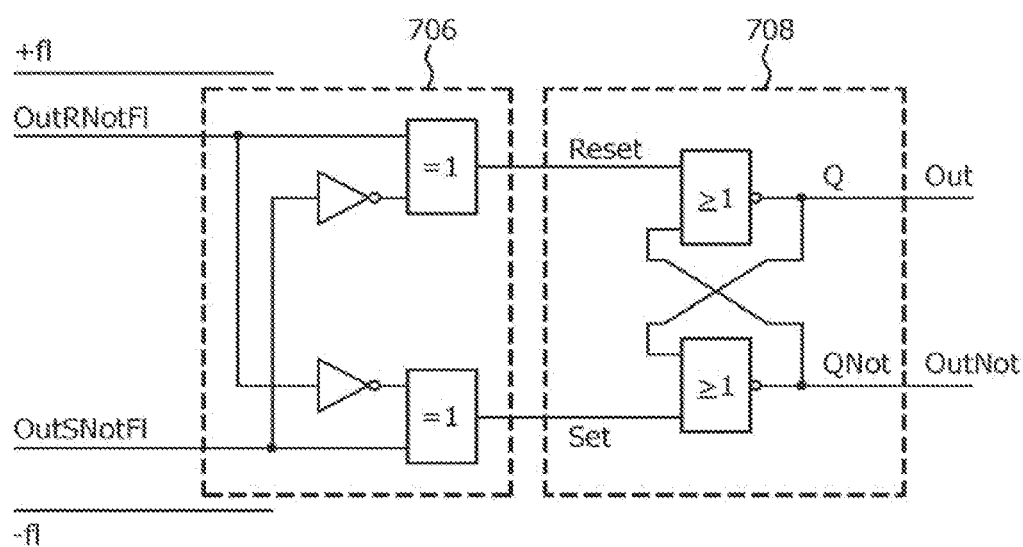

Referring to FIG. 1b, it is to be noted that the reference voltage 128 which is provided by the bi-directional switch and which is received on the reference voltage input terminal 126 may show fast and relatively large voltage swings. If the bi-directional switch is implemented as is shown in FIG. 2a, the reference voltage 128 is obtained from the common source s of the NMOS transistors M1 and M2, and therefore the reference voltage 128 is directly related to the signal that is transmitted by the bi-directional switch. Especially, in for example medical stimulators, the signals which are transmitted through the bi-directional switch may follow a wave pattern which has a relatively large amplitude. Thus, when the energy storage element is in a floating state, the voltage +fl of the first terminal and the voltage −fl of the second terminal may vary relatively quickly and may have large voltage swings. If a latch is used to memorize the state of the bi-directional witch, as for example shown in FIG. 2a, and if the latch is switched with a set and reset signal which is provided by a communication channel, which is, for example, shown in FIG. 5b, the voltages of the set and reset signal that are provided to the latch may suddenly drop or rise simultaneously. This should not lead to unwanted changes of the state of the latch and thus of state of the bidirectional switch. It is therefore advantageous, as shown in FIG. 7a, to equip the control circuit with an XOR circuitry 702 if a NAND latch 704 is used in the control circuit. If the latch is an NOR latch 708, additional circuitry 706 comprising XNOR gates may be provided in between the communication channel and the latch of the control circuit, as shown in FIG. 7b. In both circuitries of FIG. 7a and FIG. 7b, whenever both input signals OutSNotFl and OutRNotFl simultaneously drop or rise, the logic levels of the signals provided to the NAND latch 704 or the NOR latch 708 do not change. If only one of the input signals OutSNotFl and OutRNotFl increases or decreases, one of the logic levels of the signals that are provided to the NAND latch 704 or the NOR latch 708 changes. It is to be noted that in FIG. 7a and FIG. 7b the voltage rails +fl and −fl are shown, which are coupled to the first terminal and the second terminal, respectively, which indicates that the XOR circuitry 702, the NAND latch 704, the XNOR circuitry 706 and the NOR latch 708 receive the supply voltage from the voltage rails +fl and −fl. Thus, they receive a floating supply voltage when the energy storage element is in the floating state.

Figure 8:
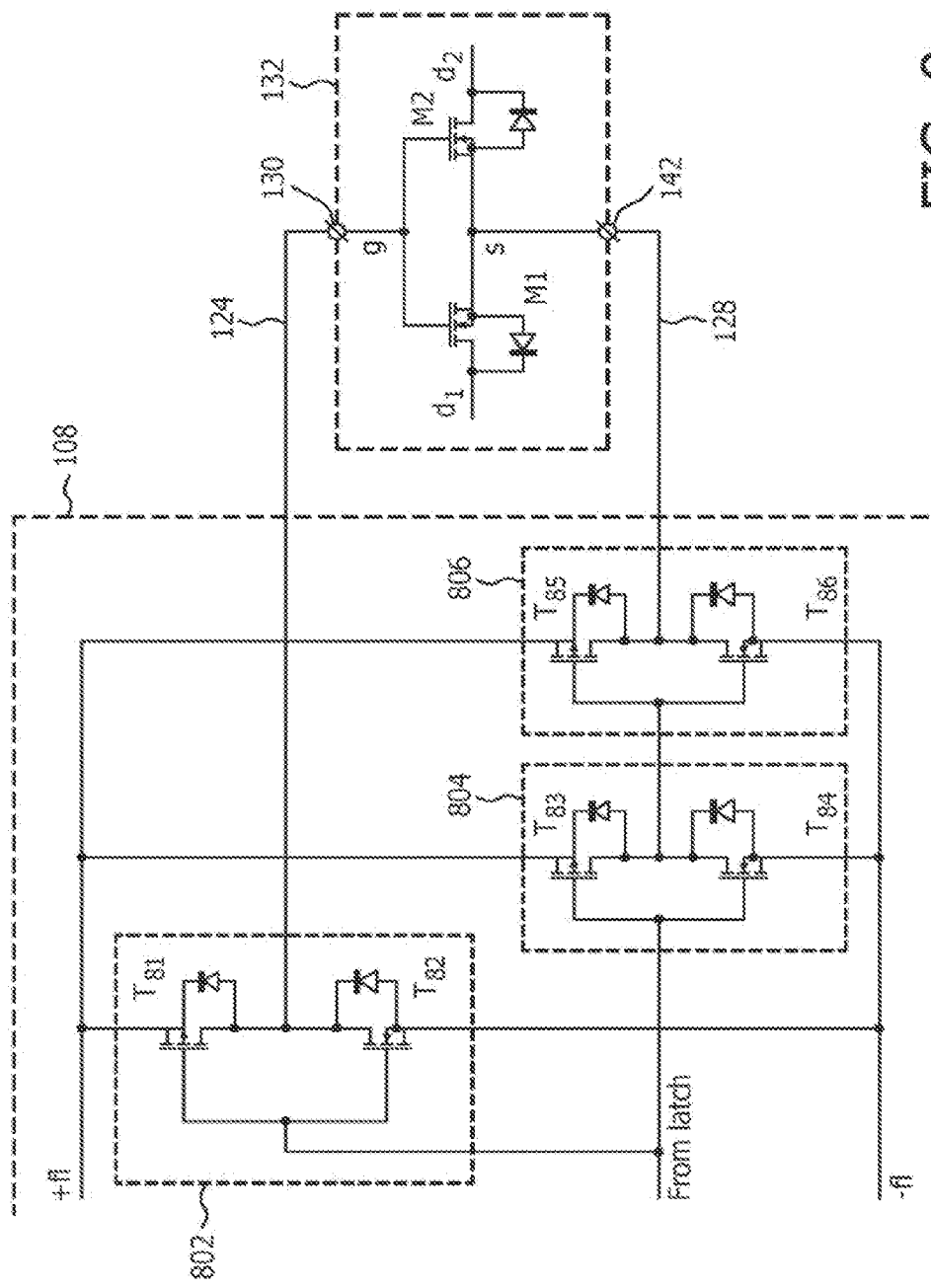

FIG. 8 shows an embodiment of an additional circuit which is comprised by the control circuit 108 and is coupled in between the latch of the control circuit 108 and the bi-directional switch 132. In this embodiment, the reference voltage 128 is coupled to the control circuit 108. The additional circuit receives a signal from the latch which indicates the on state or the off state of the bi-directional switch. This signal is fed to a first inverter 802 which comprises transistor $T_{81}$ and $T_{82}$ and is fed to a second inverter 804 comprising transistors $T_{83}$ and $T_{84}$ which is coupled in series with a third inverter 806 comprising transistors $T_{85}$ and $T_{86}$. The output of the first inverter 802 provides the control voltage 124 to the control terminal 130 of the bi-directional switch and the output of the third inverter 806 is coupled to the reference voltage output terminal 142 of the bi-directional switch. Thus, the voltage difference between the control terminal 130 and the reference voltage output terminal 142 is, depending on the state of the latch, (+fl−−fl) or −(+fl−−fl). If this voltage difference is positive, the bi-directional switch 132 is controlled to be in the on state, if the voltage difference is negative, the bi-directional switch 132 is controlled to be in the off state.

The third inverter 806 connects the reference voltage with the (floating) voltage level of the first terminal +fl or the voltage level of the second terminal −fl. Thus, the voltage level of the first terminal +fl or the voltage level of the second terminal −fl is substantially equal to the reference voltage 128, and thus is the other one of the voltage levels +fl or −fl and also relates to the reference voltage 128. The control voltage 124 is, depending on the state of the first inverter 802, equal to one of the voltage levels or +fl or −fl and, thus, the generated control voltage 124 is related to the reference voltage 128.

Figure 9:
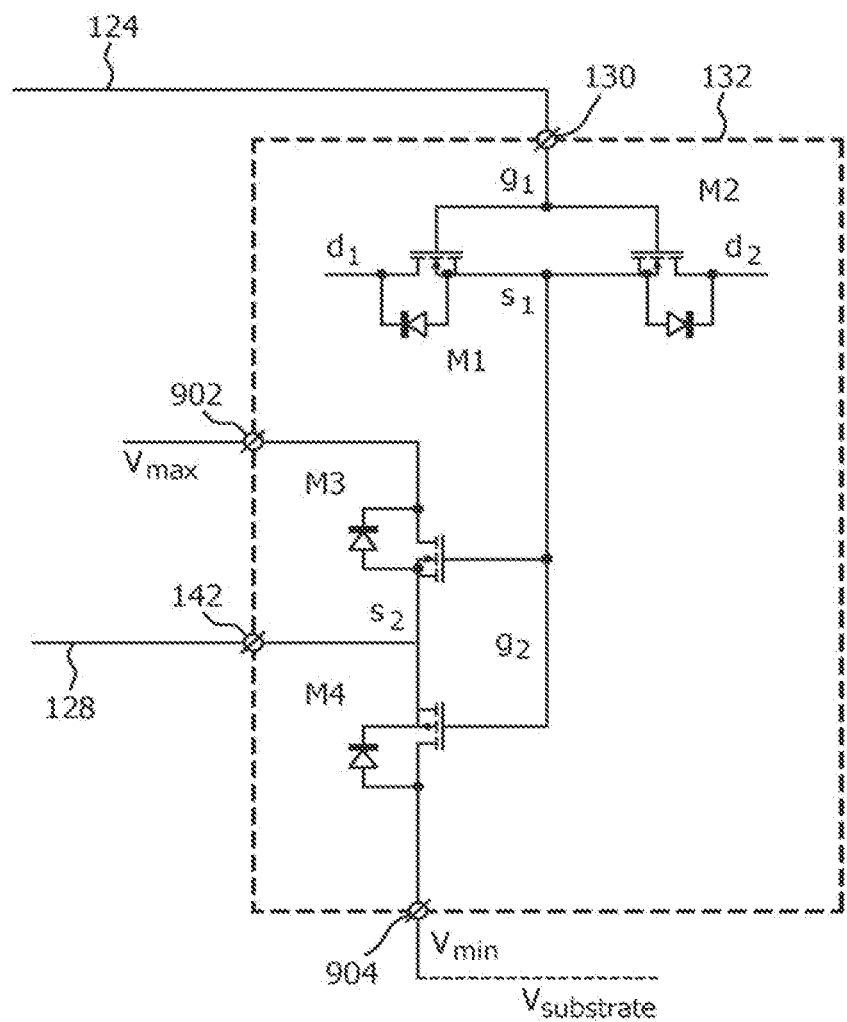

It is to be noted that in the configuration of FIG. 8, instead of connecting the common gate g to the control terminal 130, the common source s may be connected to the control terminal 130, and consequently the common gate g may be connected to the reference voltage output terminal 142. In the configuration of FIG. 8 it is only important that the difference voltage between the common gate g and the common source s is in the on state of the bi-directional switch positive and in the off stage of the bi-directional switch negative. If the common gate and the common source are connected differently as discussed in this paragraph, the OutNot output terminal of the latch has to be connected to the additional circuitry instead of the Out output terminal. FIG. 9 shows another embodiment of the bi-directional switch 132. The bi-directional main current path is in between the drain d1 of NMOS transistor M1 and drain d2 of NMOS transistor M2. The bi-directional switch 132 has two additional input terminals, namely terminal 902 which receives a voltage level $V_{max}$ which is higher than all the voltages which possibly occur in the main current path between d1 and d2, and a terminal 904 which receives a voltage level $V_{min}$ which is lower than all the voltages which possibly occur in the main current path between d1 and d2. In a practical embodiment, $V_{min}$ is the voltage of the substrate of the semiconductor device in which the bi-directional switch is manufactured. A series arrangement of an NMOS transistor M3 and a PMOS transistor M4 that have a common source $s_2$ and a common gate $g_2$ is arranged in between the terminal 902 and the terminal 904. The NMOS M3 and the PMOS M4 form a class-B circuit. Both transistors are enhancement MOSTs such that they cannot conduct simultaneously (class-B operation). The common source $s_2$ is connected to the reference voltage output terminal 142. The common source $g_2$ is connected to the common source $s_1$ of the NMOS transistors M1 and M2. The function of M3 and M4 is that the reference voltage 128 on the reference voltage output terminal gets a voltage level which is close to the voltage level of the common source $s_1$. The reference voltage 128 differs from the voltage level of the common source $s_1$ with an amount which is in a range between the threshold voltage of the NMOS transistor M3 and the threshold voltage of PMOS transistor M4. Namely, as soon as the reference voltage 128 is higher than the voltage of the common source $s_1$ (which equals the voltage of the common gate $g_2$), PMOS transistor M4 conducts until the level of the reference voltage 128 is almost equal to the voltage of the common source if the reference voltage 128 is lower than the voltage of the common source $s_1$, NMOS transistor M3 conducts until the level of the reference voltage 128 is almost equal to the voltage of the common source $s_1$.

Figure 10:
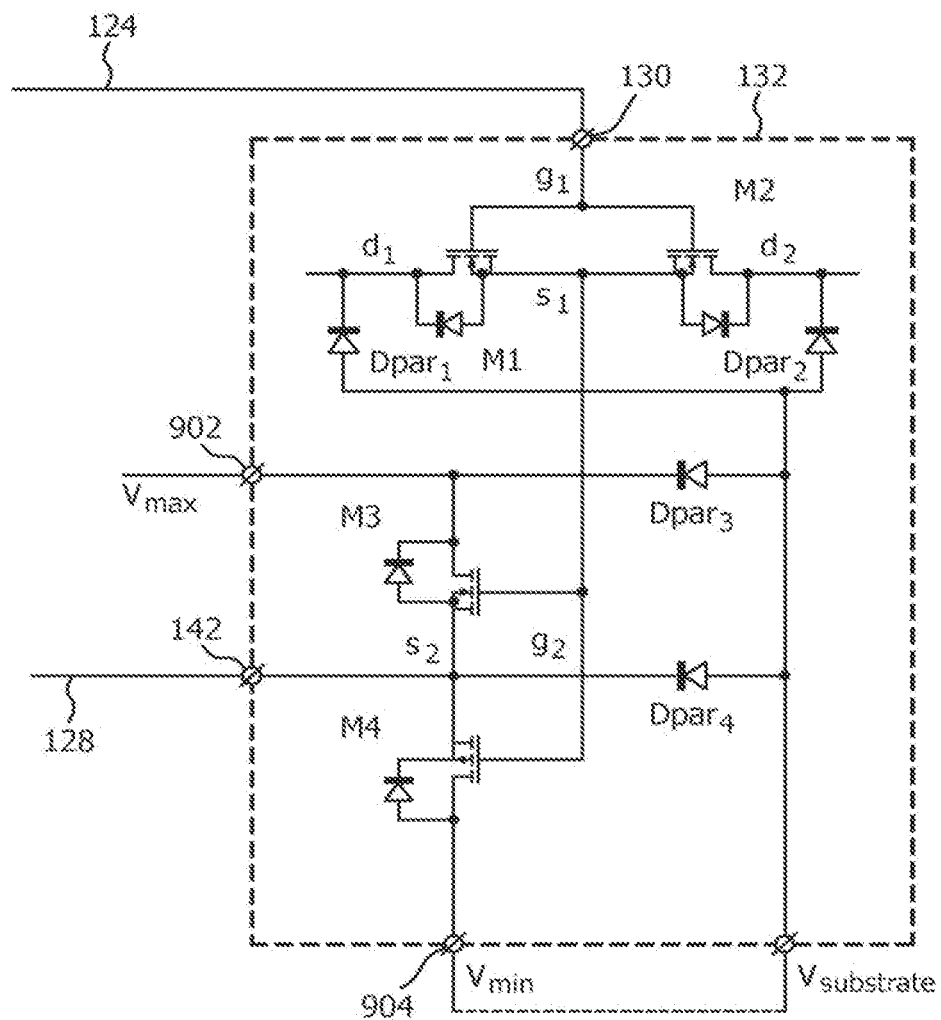

FIG. 10 schematically shows the embodiment of FIG. 9 wherein the parasitic (pn-junctions) diodes $Dpar_1 \ldots Dpar_4$ from the substrate of the semiconductor device to terminals of the transistors M1 . . . M4, respectively, are drawn.

In the discussion which follows in this paragraph, we assume that transistors M3 and M4 are not present and that the common source $s_1$ is coupled to the reference voltage output terminal 142. As discussed before, if the communication circuits 502, 504, 602, 604, 606 of FIGS. 5a, 5b, 6a, 6b, 6c communicate a set or a reset signal to a voltage level related to the voltage levels +fl and/or −fl, a current flows through the communication circuits from the voltage level +fl to the substrate of the semiconductor device on which the control circuitry (and probably the bi-directional switch is manufactured. The currents only flow for short periods of time. Further, currents always flow closed loops, and thus a part of the currents flowing through the communication channel flows from the substrate back via the parasitic diodes $Dpar_1$ and/or $Dpar_2$ to the I/O terminals of the bi-directional switch, especially when the bi-directional main current path is in the off-state. If the bi-directional main current path is in the on-state, the small currents flow through the bi-directional main current path via the circuitry which is connected to the I/O terminals of the bi-directional switch. This means that, for short periods of time, the I/O terminals of the bi-directional switch may receive a current which does not relate to the signal that has to be transmitted via the bi-directional switch. The I/O terminals of the bi-directional switch may, for example, be coupled to measurement circuits and the measurements may be disturbed by these currents.

If, as drawn in FIG. 10, MOS transistors M3 and M4 are present, the short current pulses flow in a different path. If the bi-directional switch transistors M1 and M2 are conductive, the pulses flow via the energy storage element, via transistor $T_{86}$ of inverter 806 of FIG. 8 to the reference voltage output terminal 142 and subsequently via $Dpar_4$. In the case that M3 conducts, the current loop is closed via the conductive channel of M3. If M1 and M2 are non-conductive, the current loop is closed via the transistors $T_{85}$ of inverter 806 of FIG. 8, via the reference voltage output terminal 142 and via the diode $Dpar_4$. Also in the case that M1 and M2 are non-conductive, and M3 conducts, the current loop is closed via the conductive channel of M3. Thus, the embodiment of FIG. 10 is advantageous because it prevents the disturbance of the signals on the I/O terminals of the bi-directional switch.

Figure 11:
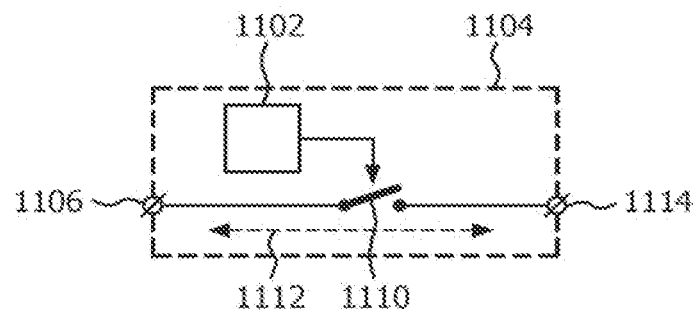

FIG. 11 schematically shows an embodiment of a bi-directional switch 1104 system according to the second aspect of the invention. The bi-directional switch system 1004 has a bi-directional main current path 1112 between a first I/O terminal 1106 and a second I/O terminal 1114. At least one semiconductor switch 1110 is provided in the bi-directional main current path 1112. The on and off state of the semiconductor switch 1110 is controlled by a control circuitry 1102. Embodiments of the semiconductor switch 1110 and of the control circuitry 1102 are discussed previously.

Figure 12:
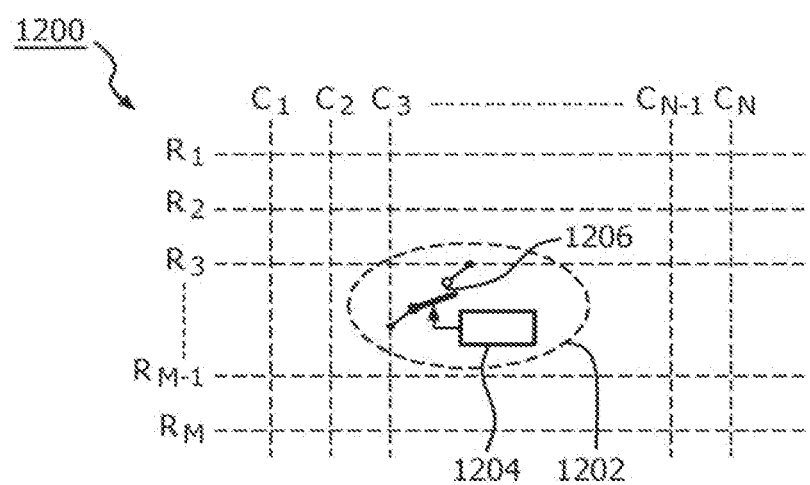

FIG. 12 schematically shows an embodiment of a switching matrix 1200. The switching matrix 1200 comprises a plurality of columns $C_1$ to $C_N$ and a plurality of rows $R_1$ to $R_M$. A bi-directional switch system 1202 is provided at at least one junction between a column $C_i$ and a row $R_j$. In the example of FIG. 12 the bi-directional switch system 1202 is provided at a junction formed by row $R_3$ and column $C_3$. The bi-directional switch system 1202 comprises a semiconductor switch 1206 and the on and off state of the semiconductor switch 1206 is controlled by a control circuitry 1204. Embodiments of the semiconductor switch 1206 and of the control circuitry 1204 are discussed previously. It should be noted that in an embodiment all the junction points of the matrix each have a bi-directional switch with a control circuitry.

Figure 13:
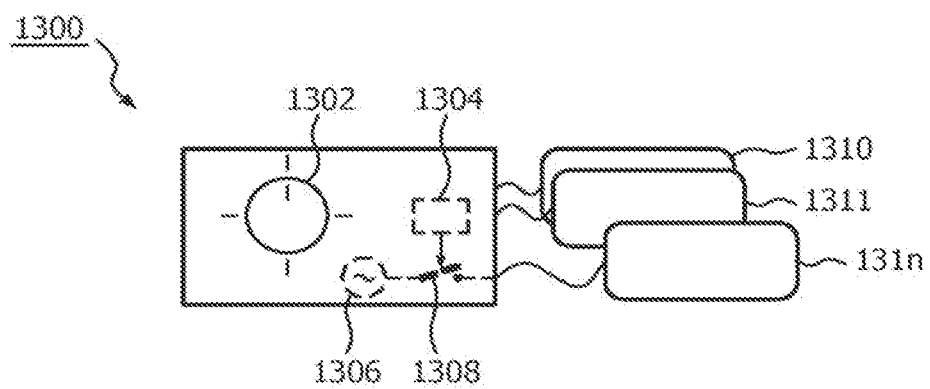

FIG. 13 schematically shows a medical stimulator 1300 according to the fourth aspect of the invention. The medical stimulator 1300 has a plurality of electrodes $1310 \ldots 131n$ which may be brought in contact with the body of a person to simulate, for examples, muscles of the person, or in another example, to provide deep brain stimulation to the person. The signal that is provided via the electrodes to the person may be selected by the user or a medical expert with a selection button 1302. Depending on the selection, a signal generator 1306 generates a signal. The signal generated by the signal generator 1306 may be connected to one of the electrodes $1310 \ldots 131n$ via a bi-directional switch. The medical stimulator 1300 comprises at least one bi-directional switch system which comprises at least one semiconductor switch 1308 in a bi-directional main current path of the bi-directional switch system. The on and off state of the bi-directional switch is controlled by a control circuitry 1304. Embodiments of the semiconductor switch 1308 and of the control circuitry 1304 are discussed previously. In another embodiment, the medical stimulator 1300 comprises a switching matrix according to the third aspect of the invention.

Figure 14:
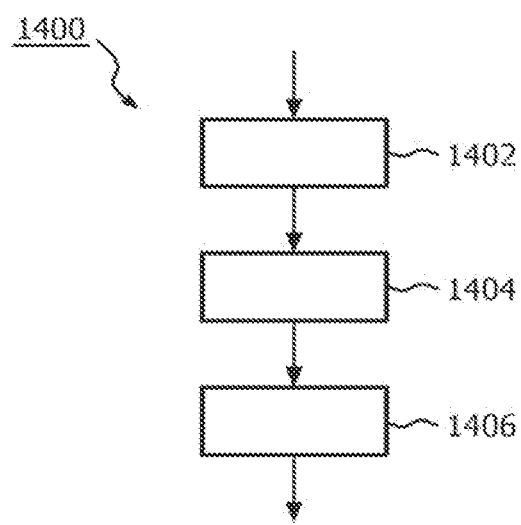

FIG. 14 schematically shows an embodiment of the method 1400 of controlling a bi-directional switch according to the fifth aspect of the invention. The bi-directional switch has a control terminal for receiving a control voltage to control an on and off state of the bi-directional switch and at least one semiconductor switch in a bi-directional main current path. The method comprises a first step of coupling 1402 by means of a coupling means an energy storage element to a supply voltage only when the bi-directional switch is in the off state for charging the energy storage element. In another step the method receives 1404 power from the energy storage element in a control circuit. In a further step the method supplies 1406 by means of the control circuit the control voltage having a voltage level being independent of the supply voltage when the energy storage element is not coupled to the supply voltage.

It is to be noted that the control circuitry according to the first aspect of the invention, the bi-directional switch system, a switching matrix, or the method according to the fifth aspect of the invention may be used in a plurality of applications. A first example are medical implants which include a cross point switch matrix to couple internal circuitry to external probes both for stimulation and/or recording, such as Deep Brain Stimulators or Pace Makers. In a second example, in telephony, a circuitry near or within the Subscriber Line Interface Circuit couples the subscriber telephone line to the internal circuitry of a telephone exchange using for example a cross-point switch matrix. In a third example, integrated display drivers use supply voltages of a few tens of volts, which may be switched via a bi-directional main current path of a bi-directional switch. In a fourth example, a cross-point switch matrix could be used to couple various piezo elements to piezo drivers integrated in a CMOS technology. In a fifth example, LEDs for lighting applications are often arranged in series to form LED strings and the voltage to supply power to the LED strings may be switched via a bi-directional switch system. In a sixth example, advanced power supply conversion systems require bi-directional switches for increased functionality and/or efficiency.

It should be noted that the above-mentioned embodiments illustrate rather than limit the invention, and that those skilled in the art will be able to design many alternative embodiments without departing from the scope of the appended claims.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A method comprising:
   coupling, while a switch is in an off state, an energy storage element to a supply voltage to charge the energy storage element;
   transitioning the switch from the off state to an on state by at least:
      decoupling the energy storage element from the supply voltage such that a voltage level of the energy storage element floats with respect to the supply voltage; and
      outputting, while the energy storage element is decoupled from the supply voltage and using power from the energy storage element, a control signal to the switch, the control signal having a voltage level that is effective to enable switching of the switch and is independent of the supply voltage.

2. The method of claim 1, wherein transitioning the switch from the off state to the on state further comprises:
   receiving, from the switch, a reference voltage that indicates a voltage level of the control signal that is effective to enable switching of the switch.

3. The method of claim 1, wherein the switch is a bi-directional switch.

4. The method of claim 3, wherein the switch is included in a switch matrix.

5. A medical device comprising:
   an energy storage element;
   a switch having a first state and a second state controlled by a control signal; and
   a control circuit configured to generate, using power from the energy storage element, the control signal at a voltage level that is effective to enable switching of the switch and is independent from a voltage level of a power supply used to charge the energy storage element, wherein the control circuit is further configured to decouple the energy storage element from the power supply when generating the control signal.

6. The medical device of claim 5, wherein the switch is a bi-directional switch.

7. The medical device of claim 5, wherein
   the control circuit further comprises a reference voltage input terminal to receive a reference voltage, and
   the switch further comprises a reference voltage output terminal configured to provide the reference voltage to the reference voltage input terminal, wherein the reference voltage indicates a voltage level of the control signal that is effective to enable switching of the switch.

8. The medical device of claim 7, wherein the control circuit further comprises a latch configured to memorize a state of the switch and to supply the control signal based on the memorized state.

9. The medical device of claim 5, wherein the switch is included to a switch matrix.

10. A medical device comprising:
    means for coupling, while a switch is in an off state, an energy storage element to a supply voltage to charge the energy storage element;
    means for transitioning the switch from the off state to an on state, wherein the means for transitioning comprise:
       means for decoupling the energy storage element from the supply voltage such that a voltage level of the energy storage element floats with respect to the supply voltage; and
       means for outputting, while the energy storage element is decoupled from the supply voltage and using power from the energy storage element; a control signal to the switch, the control signal having a voltage level that is effective to enable switching of the switch and is independent of the supply voltage.

11. The medical device of claim 10, wherein the switch is a bi-directional switch.

12. The medical device of claim 10, wherein the means for transitioning the switch from the off state to the on state further comprise:
    means for receiving, from the switch, a reference voltage that indicates a voltage level that is effective to enable switching of the switch.

13. The medical device of claim 10, wherein the switch is included in a switch matrix.

* * * * *